United States Patent [19]

Pratt et al.

[11] Patent Number: 5,656,647

[45] Date of Patent: Aug. 12, 1997

[54] APPLICATION OF RILUZOLE FOR PROMOTING RESTORATION FOLLOWING RADIATION

[75] Inventors: Jeremy Pratt, Charenton Le Pont; Jean-Marie Stutzmann, Villecresnes, both of France

[73] Assignee: Rhone-Poulenc Rorer S.A., Antony, France

[21] Appl. No.: 446,733

[22] PCT Filed: Jan. 3, 1994

[86] PCT No.: PCT/FR94/00002

§ 371 Date: Jun. 6, 1995

§ 102(e) Date: Jun. 6, 1995

[87] PCT Pub. No.: WO94/15600

PCT Pub. Date: Jul. 21, 1994

[30] Foreign Application Priority Data

Jan. 7, 1993 [FR] France .................................. 93 00073

[51] Int. Cl.$^6$ .................................................. A61K 31/425
[52] U.S. Cl. ............................................. 514/367; 514/917
[58] Field of Search ...................................... 514/367, 917

[56] References Cited

U.S. PATENT DOCUMENTS 4,370,338  1/1983  Mizoule .
4,826,860  5/1989  Johnson et al. .
4,918,090  4/1990  Johnson et al. .
5,236,940  8/1993  Audiau et al. ............................ 514/367
5,240,948  8/1993  Gueremy et al. .

FOREIGN PATENT DOCUMENTS 0 050 551    4/1982   European Pat. Off. .
0 282 971    9/1988   European Pat. Off. .
WO91/17984  11/1991   WIPO .

OTHER PUBLICATIONS

J. Neurosci., vol. 9, No. 11, 1989, pp. 3720–3727, C. Malgouris et al., "Riluzole, a Novel Antiglutamate, Prevents Memory Loss . . . ".

Database WPI, Week 8511, Derwent Publications Ltd., London, GB.

*Primary Examiner*—James H. Reamer
*Attorney, Agent, or Firm*—Finnegan, Henderson, Farabow, Garrett & Dunner, L.L.P.

[57] ABSTRACT

This invention relates to an application of riluzole or its pharmaceutically acceptable salts in the preparation of drugs having radiorestoring properties.

4 Claims, No Drawings

APPLICATION OF RILUZOLE FOR PROMOTING RESTORATION FOLLOWING RADIATION

FIELD OF THE INVENTION

The present invention relates to a novel therapeutic application of riluzole (6-trifluoro-methoxy-2-aminobenzothiazole) or the pharmaceutically acceptable salts of this compound.

BACKGROUND OF THE INVENTION

Riluzole is useful as an anticonvulsant, anxiolytic and hypnotic medicinal product (Patent EP 50,551), in the treatment of schizophrenia (EP 305,276), in the treatment of sleep disorders and depression (EP 305,277), in the treatment of cerebrovascular disorders and as an anaesthetic (EP 282,971).

DESCRIPTION OF THE INVENTION

It has now been found, surprisingly, that this compound may also be used to promote restoration following radiation.

Restoration following radiation is useful in X-ray therapy, in particular in the treatment of cancers, and against other sources of harmful radiation such as those encountered by persons in areas in the vicinity of nuclear explosions.

EXAMPLES

The activity of the product has been demonstrated on the rhinencephalon of young rats subjected to an overall gamma irradiation.

Irradiation is performed by means of a gamma ray source, cobalt-60.

The animals used are 15-day-old male Sprague-Dawley strain rats weighing 28 to 33 g, which are placed in an aerated Plexiglass restraining box undergoing a rotation of 180° in order to carry out homogeneous overall irradiations in a single dose of 1.5 and 2.5 Gy, the dose rate of which is 0.2 Gy per minute. The survival time between irradiation and sacrifice is 6 hours. All the animals are fixed by intra-aortic perfusion of a fixative fluid composed of 1% of paraformaldehyde, 1% of glutaraldehyde and 0.05% of calcium chloride in 0.4M phosphate buffer, pH 7.3. To prevent coagulation, 0.04 ml of heparin is injected into the ventricle, and 0.3 ml of 1% sodium nitrite to clear the vessels of red cells.

The animals are anaesthetized by intraperitoneal injection of 3% pentobarbitone sodium. The animals are then laid on their back and fixed to the operating table. The thoracic cage is opened and held open by means of 2 clamps. The heart is thus exposed, the tip of the left ventricle is incised and the perfusion cannula is introduced up to the beginning of the arch of the aorta and clamped. The right atrium is incised and perfusion is performed. Inflow of the perfusion fluid is effected under gravity. After perfusion, the animal's head is cut off and the brain is removed, immersed in fixative fluid and stored overnight at 4° C.

On the day following perfusion, frontal sections of the gyrus dentatus are cut under a binocular magnifier. The fragments collected are immersed in the washing fluid for 5 minutes. They are then dehydrated in alcohol baths of increasing concentration and thereafter included in Araldite. 1-micrometer semi-thin sections are prepared using a Reichert ultramicrotome with glass knives. They are stained in the heated state with a filtered 1% solution of toluidine blue prepared in 1% borate buffer, and then observed using an Orthoplan microscope.

The comparative study consists in counting on 3 non-serial sections (separated by 10 micrometers each) for each rat and on an aggregate of 1000 cells (granular and subgranular) in total. The number of pyknotic cells is counted, and then the number of surviving cells observed in this area. This enables the percentage of surviving cells relative to the number of cells in the area to be calculated (percentage survival=100×living cells/living cells+pyknotic cells).

The product under study is administered intraperitoneally at doses of 1, 2, 4 and 8 mg/kg, 20 minutes after irradiation (at the beginning of pyknosis).

The results obtained are recorded in the following tables, and show that, after treatment with the test product, neuronal degeneration is less than in irradiated controls not receiving a product.

TEST 1

| IRRADIATION | CONTROLS CELLULAR SURVIVAL | RILUZOLE (2 mg/kg) CELLULAR SURVIVAL |
|---|---|---|
| 1.5 Gy | 88.8% | 91.2% |
| 2.5 Gy | 87.1% | 92.2% |

TEST 2

| IRRADIATION | CONTROLS CELLULAR SURVIVAL | RILUZOLE 1 mg/kg CELLULAR SURVIVAL | RILUZOLE 2 mg/kg CELLULAR SURVIVAL | RILUZOLE 4 mg/kg CELLULAR SURVIVAL | RILUZOLE 8 mg/kg CELLULAR SURVIVAL |
|---|---|---|---|---|---|
| 2.5 Gy | 75.35 ± 2.4% | 81.99 ± 2.32% | 83.54 ± 1.96% | 86.07 ± 2.78 | 85.41 ± 2.14% |

As pharmaceutically acceptable salts, the addition salts with inorganic acids, such as hydrochloride, sulphate, nitrate or phosphate, or organic acids, such as acetate, propionate, succinate, oxalate, benzoate, fumarate, maleate, methanesulphonate, isethionate, theophyllineacetate, salicylate, phenolphthalinate or methylenebis(β-hydroxynaphthoate), or substitution derivatives of these derivatives, may be mentioned in particular.

The medicinal products consist at least of riluzole, in free form or in the form of an addition salt with a pharmaceutically acceptable acid, in the pure state or in the form of a composition in which it is combined with any other pharmaceutically compatible product, which may be inert or physiologically active. The medicinal products according to the invention may be employed orally or parenterally.

As solid compositions for oral administration, tablets, pills, powders (gelatin capsules, wafer capsules) or granules may be used. In these compositions, the active principle according to the invention is mixed with one or more inert diluents such as starch, cellulose, sucrose, lactose or silica, under a stream of argon. These compositions can also comprise substances other than diluents, for example one or more lubricants such as magnesium stearate or talc, a colouring, a coating (dragées) or a varnish.

As liquid compositions for oral administration, pharmaceutically acceptable solutions, suspensions, emulsions, syrups and elixirs may be used, containing inert diluents such as water, ethanol, glycerol, vegetable oils or liquid paraffin. These compositions can comprise substances other than diluents, for example wetting, sweetening, thickening, flavouring or stabilizing products.

The sterile compositions for parenteral administration can preferably be solutions, aqueous or non-aqueous, suspensions or emulsions. As a solvent or vehicle, water, propylene glycol, a polyethylene glycol, vegetable oils, especially olive oil, injectable organic esters, for example ethyl oleate, or other suitable organic solvents may be employed. These compositions can also contain adjuvants, especially wetting, tonicity, emulsifying, dispersing and stabilizing agents. The sterilization may be carried out in several ways, for example by aseptic filtration, by incorporation of sterilizing agents in the composition, by irradiation or by heating. They may also be prepared in the form of sterile solid compositions which can be dissolved at the time of use in sterile water or any other sterile injectable medium.

The doses depend on the effect sought, the treatment period and the administration route used; they are generally between 50 and 800 mg per day via the oral route for an adult, with single doses ranging from 25 to 200 mg of active substance, and between 25 and 600 mg per day via the intravenous route for an adult, with single doses ranging from 12.5 to 200 mg of active substance.

Generally speaking, the doctor will determine the appropriate dosage in accordance with the age, the weight and all other factors specific to the subject to be treated.

The examples which follow illustrate medicinal products according to the invention:

EXAMPLE A

Tablets containing a 50 mg dose of active product and having the following composition are prepared according to the usual technique:

| | |
|---|---|
| Riluzole | 50 mg |
| Mannitol | 64 mg |
| Microcrystalline cellulose | 50 mg |
| Povidone excipient | 12 mg |
| Sodium carboxymethylstarch | 16 mg |
| Talc | 4 mg |
| Magnesium stearate | 2 mg |
| Colloidal silica, anhydrous | 2 mg |
| Mixture of methylhydroxypropyl-cellulose, polyethylene glycol 6000 and titanium dioxide (72:3.5:24.5) | |
| q.s. 1 finished film-coated tablet weighing 245 mg | |

EXAMPLE B

Hard gelatin capsules containing a 50 mg dose of active product and having the following composition are prepared according to the usual technique:

| | |
|---|---|
| Riluzole | 50 mg |
| Cellulose | 18 mg |
| Lactose | 55 mg |
| Colloidal silica | 1 mg |
| Sodium carboxymethylstarch | 10 mg |
| Talc | 10 mg |
| Magnesium stearate | 1 mg |

EXAMPLE C

An injection containing 10 mg of active product and having the following composition is prepared:

| | |
|---|---|
| Riluzole | 10 mg |
| Benzoic acid | 80 mg |
| Benzyl alcohol | 0.06 cm$^3$ |
| Sodium benzoate | 80 mg |
| Ethanol, 95% | 0.4 cm$^3$ |
| Sodium hydroxide | 24 mg |
| Propylene glycol | 1.6 cm$^3$ |
| Water | q.s. 4 cm$^3$ |

The invention also relates to the process for preparing medicinal products which can be used to promote restoration following radiation, consisting in mixing riluzole or the pharmaceutically acceptable salts of this compound with one or more compatible and pharmaceutically acceptable diluents and/or adjuvants.

The invention also relates to a method for treating a mammal, and in particular man, requiring restoration following radiation, comprising the administration of an effective amount of riluzole or the pharmaceutically acceptable salts of this compound.

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The above references are hereby incorporated by reference.

We claim:

1. A method for promoting cellular restoration following irradiation, said method comprising the step of administering to a patient in recognized need of such restorative treatment an amount of riluzole or a pharmaceutically acceptable salt thereof effective for promoting said cellular restoration following irradiation, wherein said riluzole is administered to said patient after the patient has been irradiated.

2. A method according to claim 1, wherein riluzole is administered orally at a dosage of 50 to 800 mg per day.

3. A method according to claim 1, wherein riluzole is administered intravenously at a dosage of 25 to 600 mg per day.

4. A method according to claim 1, wherein said riluzole or said pharmaceutically acceptable salt thereof is mixed with at least one compatible and pharmaceutically acceptable diluent or adjuvant or both.

* * * * *